(12) United States Patent
Goebel et al.

(10) Patent No.: US 8,759,564 B2
(45) Date of Patent: Jun. 24, 2014

(54) AMIDOACETONITRILE COMPOUNDS HAVING PESTICIDAL ACTIVITY

(75) Inventors: Thomas Goebel, Lörrach (DE); Noëlle Gauvry, Kembs (FR); Heinz Sager, Wohlen (CH)

(73) Assignee: Novartis AG, Basel (CH)

( * ) Notice: Subject to any disclaimer, the term of this patent is extended or adjusted under 35 U.S.C. 154(b) by 92 days.

(21) Appl. No.: 13/510,006

(22) PCT Filed: Nov. 22, 2010

(86) PCT No.: PCT/EP2010/067924
§ 371 (c)(1),
(2), (4) Date: May 16, 2012

(87) PCT Pub. No.: WO2011/061326
PCT Pub. Date: May 26, 2011

(65) Prior Publication Data
US 2012/0232138 A1    Sep. 13, 2012

(30) Foreign Application Priority Data
Nov. 23, 2009   (EP) .................................... 09176738

(51) Int. Cl.
*C07C 255/60* (2006.01)
*A01N 37/34* (2006.01)

(52) U.S. Cl.
USPC ............................ 558/415; 558/413; 514/522

(58) Field of Classification Search
USPC .................................. 558/413, 415; 514/522
See application file for complete search history.

(56) References Cited

U.S. PATENT DOCUMENTS

| | | | |
|---|---|---|---|
| 7,705,047 B2 * | 4/2010 | Goebel et al. .................. 514/521 |
| 8,168,681 B2 * | 5/2012 | Gauvry et al. ................ 514/618 |
| 2005/0203178 A1 | 9/2005 | Ducray et al. | |
| 2007/0037881 A1 | 2/2007 | Goebel et al. | |

OTHER PUBLICATIONS

ISR, 2011.
Written Opinion, 2011.

* cited by examiner

*Primary Examiner* — Shailendra Kumar
(74) *Attorney, Agent, or Firm* — Ann R. Pokasky, Esq.; Dilworth & Barrese, LLP

(57) ABSTRACT

Novel amidoacetonitrile compounds and compositions containing the compounds are disclosed. The compounds have pesticidal properties and are suitable for controlling endoparasites on warm-blooded animals.

11 Claims, No Drawings

AMIDOACETONITRILE COMPOUNDS HAVING PESTICIDAL ACTIVITY

CROSS-REFERENCE TO RELATED APPLICATIONS

This application claims priority to PCT Application Number PCT/EP2010/067924, filed Nov. 22, 2010, which claims priority to EP Application Number 09176738.4, filed Nov. 23, 2009.

The present invention relates to new amidoacetonitrile compounds of formula

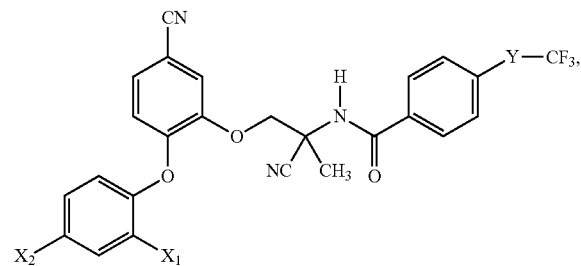

I wherein
$X_1$ is halogen;
$X_2$ is $CF_3$, $OCF_3$, $SCF_3$, $S(O)CF_3$, $S(O_2)CF_g$, or $SF_5$, and
Y is G, S, S(O) or $S(O_2)$,
each respectively in free form or in salt form, their preparation and usage in the control of endo- and ectoparasites, especially helminths, in and on warm-blooded animals, especially productive livestock and domestic animals, as well as on plants, furthermore pesticides which contain at least one of these compounds.

Substituted amidoacetonitrile compounds having pesticidal activity are described, for example, in WO 2003/104187 or WO 2005/58802, However, the active ingredients specifically disclosed therein cannot always fulfil the requirements regarding potency and activity spectrum. There Is therefore a need for active ingredients with improved pesticidal properties. It has now been found that the amidoacetonitrile compounds of formula I have excellent pesticidal properties, especially against endo- and ectoparasites in and on warm-blooded animals and plants.

Within the compounds of formula I the following meanings and preferences apply. Halogen is, for example, fluorine, chlorine, bromine or Iodine, especially fluorine, chlorine or bromine, in particular chlorine.
$X_1$ is preferably fluorine (F), chlorine (Cl) or bromine (Br), in particular Cl.
$X_2$ is preferably $CF_3$ or $OCF_3$, in particular $OCF_3$,
Y is preferably O, S or $S(O_2)$, in particular O or $S(O_2)$.
Preferred embodiments are, for example:
(i) A compound of formula I above, wherein $X_1$ is halogen, $X_2$ is $CF_3$ or $OCF_3$, and Y is O, S, S(O) or $S(O_2)$,
(ii) A compound of formula I above, wherein $X_3$ is Cl, $X_2$ is $CF_3$ or $OCF_3$, and Y is O, S or $S(O_2)$.
(ii) A compound of formula I above, wherein $X_1$ t is Cl, $X_2$ is $OCF_3$, and Y is O, S S(O) or $S(O_2)$.
(iii) A compound of formula I above, wherein $X_1$ is Cl, $X_2$ is $OCF_3$, and Y is O or $S(O_2)$.

The compounds of the present invention have an asymmetric carbon atom in the 1-position labelled with (1*) in the formula I' below

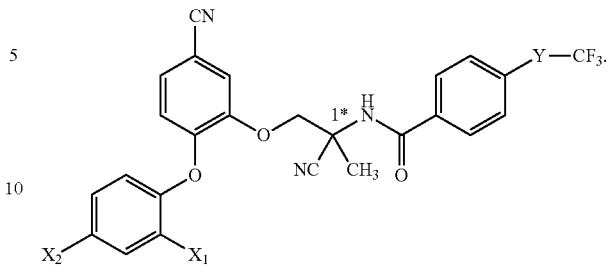

I'

Accordingly, the compounds of formula I may exist as optical isomers. The present invention includes individual enantiomers of the compounds of formula I and mixtures thereof, including racemates. In addition, it has been found that following the separation of the racemates Into the two pure enantiomers by standard methods, a, g. by chemical resolution using optically active acid or base or by chromatography on chiral adsorbents, e.g. high-pressure liquid chromatography on acetyl cellulose, or by the process as disclosed in WO 2008/50887, one of them has proven to be biologically less active (the distomer), whereas the other enantiomer is highly bioactive (the eutomer). In general, the (1S)-enantiomers of the formula (I') are highly bioactive, whereas the (1R)-enantiomers are less bioactive.

The compounds of formula I may exist in more than one tautomeric form. The present invention encompasses all tautomers, as well as mixtures thereof.

Certain compounds of formula I may be able to form salts with acids or bases. The present invention includes said compounds of formula I in form of a salt to the extent that they are pharmaceutical or veterinarily acceptable.

The compounds of formula I and their salts may exist in unsolvated or solvated forms. The term solvate herein describes a molecular complex comprising the compound of formula I and one or more pharmaceutically or veterinarily acceptable solvents, for example ethanol or water. In case of water. The term "hydrate" is used.

Preferred embodiments within the scope of the invention are:
(1) A compound of formula I above, wherein $X_1$ is F, Cl or Br, $X_2$ is $CF_3$ or $OCF_3$ and Y is O, S, S(O) or $S(O_2)$;
(2) A compound of formula I above, wherein $X_1$ is Cl, $X_2$ is $OCF_3$ and Y is O or $S(O_2)$;
(3) A compound of formula I, which is N-[1-cyano-2-(5-cyano-2-{2-chloro-4-trifluoromethoxy-phenoxy}-phenoxy)-1-methylethyl]-4-trifluoromethoxybenzamide;
(4) A compound of formula I, which is N-[1-cyano-2-(5-cyano-2-{2-chloro-4-trifluoromethoxy-phenoxy}-phenoxy)-1-methylethyl]-4-trifluoromethylsulfonylbenzamide;
(5) A compound of formula I, which is N-[1-cyano-2-(5-cyano-2-{2-chloro-4-trifluoromethoxy-phenoxy}-phenoxy)-1-methylethyl]-4-trifluoromethylsulfonylbenzamide;
(6) A compound of formula I, which is N-[1-cyano-2-(5-cyano-2-{2-chloro-4-trifluoromethoxy-phenoxy}-phenoxy)-1-methylethyl]-4-trifluoromethylsulfonylbenzamide;
(7) The (1S)-enantiomer of each of the compounds mentioned in items (1)-(6) above;
(8) The enantiomer N-[(1S)-1-cyano-2-(5-cyano-2-{2-chloro-4-trifluoromethoxyphenoxy}-phenoxy)-1-methylethyl]-4-trifluoromethoxybenzamide;

(9) The enantiomer N-[(1S)-1-cyano-2-(5-cyano-2-{2-chloro-4-trifluoromethoxyphenoxy}-phenoxy)-1-methyl-ethyl]-4-trifluoromethylsulfonylbenzamide.

The compounds of the present invention may be prepared, for example, in analogy to the processes as disclosed in WO 2003/104187 or WO 2005/58802.

Salts of compounds I may be produced in known manner. Acid addition salts of compounds I, for example, are obtainable by treatment with a suitable acid or a suitable ion exchange reagent, and salts with bases are obtainable by treatment with a suitable base or a suitable Ion exchange reagent.

Salts of compounds I can be converted Info the free compounds I by the usual means, acid addition salts e.g. by treating with a suitable basic composition or with a suitable ion exchange reagent, and salts with bases e.g. by treating with a suitable acid or a suitable ion exchange reagent.

Salts of compounds I can be converted into, other salts of compounds I in a known manner; acid addition salts can be converted for example info other acid addition salts, e.g. by treating a salt of an inorganic acid, such as a hydrochloride, with a suitable metal salt, such as a sodium, barium, or sliver salt, of an acid, e.g. with silver acetate, in a suitable solvent, in which a resulting inorganic salt, e.g. silver chloride, is insoluble and thus precipitates out from the reaction mixture.

Depending on the method and/or reaction conditions, compounds I with salt-forming characteristics can be obtained in free form or in the form of sails.

Compounds I can also be obtained in the form of their hydrates and/or also can include other solvents, used for example where necessary for the crystallisation of compounds present in solid form.

As mentioned before, the compounds of formula I may he optionally present as optical and/or geometric isomers or as a mixture thereof. The invention relates both to the pure isomers and to all possible isomeric mixtures, and is hereinbefore and hereinafter understood as doing so, even if stereochemical details are not specifically mentioned in every case.

Diastereoisomeric mixtures of compounds of formula I, which are obtainable by the process or in another way, may be separated in known manner, on the basis of the physical-chemical differences in their components, into the pure diasteraoisomers, for example by fractional crystallisation, distillation and/or chromatography.

Splitting of mixtures of enantiomers, that are obtainable accordingly, into the pure isomers, may be achieved by known methods, for example by recrystallisation from an optically-active. solvent, by chromatography on chiral adsorbents, e.g. high-pressure liquid chromatography (HPtC) on acetyl cellulose, with the assistance of appropriate microorganisms, by cleavage with specific immobilised enzymes, through the formation of inclusion compounds, e.g. using chiral crown ethers, whereby only one enantiomer is complexed. A preferred process for enantiomer separation is disclosed in WO 2008/50887.

The compounds I according to the invention are notable for their broad activity spectrum and are valuable active ingredients for use in pest control, including in particular the control of endo- and ectoparasites, especially helminths, in and on warm-blooded animals, especially livestock and domestic animals, whilst being well-tolerated by warm-blooded animals and fish.

In the context of the present invention, ectoparasites are understood to be in particular insects, mites and ticks. These include insects of the order: Lepidoptera, Coleoptera, Homoptera, Heteroptera, Diptera, Thysanoptera, Orthoptera, Anoplura, Siphonaptera, Mallophaga, Thysanura, Isoptera, Psocopteraand Hymenoptera. However, the ectoparasites which may be mentioned in particular are those which trouble humans or animals and carry pathogens, for example flies such as *Musca domestica, Musca vetustissima, Musca autumnalis, Fannia canicularis, Sarcophaga carnaria, Lucilia cuprina, Hypoderma bovis, Hypoderma lineatum, Chrysomyia chloropyga, Dermatobia hominis, Cochliomyia hominivorax, Gasterophilus intestinalis, Oestrus ovis, Stomoxys calcitrans, Haematobia irritans* and midges (*Nematocera*), such as *Culicidae, Simuliidae, Psychodidae*, but also blood-sucking parasites, for example fleas, such as *Ctenocephalides talis* and *Ctenocephalides canis* (cat and dog fleas), *Xenopsylia cheopis, Pulex irritans, Dermatophilus penetrans*, lice, such as *Damalina ovis, Pediculus humanis*, biting flies and horse-flies (*Tabanidae*), *Haematopota*-spp. such as *Haematopota pluvialis, Tabanidea* spp. such as *Tabanus nigrovittatus, Chrysopsinae* spp. such as *Chrysops caecutiens*, tsetse flies, such as species of *Glossinia*, biting insects, particularly cockroaches, such as *Blatella germanica, Blatta orientalis, Periplaneta americana*, mites, such as *Dermanyssus gallinae, Sarcoptes scabiei, Psoroptes ovis* and *Psorergates* spp, and last but not least ticks. The latter belong to the order *Acarina*. Known representatives of ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest warm-blooded animals including farm animals, such as cattle, pigs, sheep and goats, poultry such as chickens, turkeys and geese, fur-bearing animals such as mink, foxes, chinchillas, rabbits and the like, as well as domestic animals such as cats and. dogs, but also humans.

The compounds I according to the invention are also active against all or Individual development stages of animal pests showing normal sensitivity, as well as those showing resistance, such as insects and members of the order Acarina. The insecticidal, ovicidal and/or acaricidal effect of the active substances of the Invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

Compounds I can also he used against hygiene pests, especially of the order Diptera of the families Sarcophagidae, Anophilidae and Culicidae ; the orders Orthoptera, Dictyopiera (e.g. the family Blattidae) and Hymenoptera (e.g. the family Formicidae).

In particular, the compounds are effective against helminths, in which the endoparasitic nematodes and trematodes may he the cause of serious diseases of mammals and poultry, e.g. sheep, pigs, goats, cattle, horses, donkeys, dogs, cats, guinea-pigs or exotic birds, in particular sheep or especially cattle. Typical nematodes of this indication are: *Haemonchus, Trichostrongyius, Qstertagia, Nemaiodirus, Cooperia, Ascaris, Bunostonum, Oesophago-stonum, Charbmiia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. The trematodes include, in particular, the family of Fasciolideae, especially *Fasciola hepatica*.

It could also be shown surprisingly and unexpectedly that the compounds of formula I have exceptionally high efficacy against nematodes that are resistant to many active substances. This can be demonstrated in vitro by the LDA test and in vivo for example in Mongolian gerbils and sheep. It was shown that amounts of active substance which kill sensitive strains of *Haemonchus contortus* or *Trichostrongyius colubriformis*, are also sufficiently effective at controlling corresponding strains that are resistant to benzimidazoles, levamisoie and macrocyclic lactones (for example ivermectin).

Certain pests of the species *Nematodirus, Cooperia* and *Oesophagostonum* infest, the intestinal tract of the host animal, while others of the species *Haemonchus* and *Qstertagia* are parasitic in the stomach and those of the species *Dictyocaulus* are parasitic in the lung tissue. Parasites of the families Filariidae and Setariidae may be found in the infernal cell tissue and in the organs, e.g. the heart, the blood vessels, the lymph vessels and the subcutaneous tissue, A particularly notable parasite is the heartworm of the dog, *Dirofilaria immitis*. The compounds of formula I are highly effective against these parasites. The pests which may be controlled by the compounds of formula I also include those from the class of Castoda (tapeworms), e.g, the families Mesocestoidae, especially of the genus *Mesocestoides*, in particular *M. lineatus; Dilepidide*, especially *Dipylidium caninum, Joyeuxiella* spp,, in particular *Joyeuxiella pasquaii*, and *Diplopylidium* spp. and *Taeniidae*, especially *Taenia pisiformis, Taenia cervi, Taenia ovis, Taneia hydatigena, Taenia multiceps, Taenia taeniaeformis, Taenia serialis*, and *Echinocuccus* spp., most preferably *Taneia hydatigena, Taenia ovis, Taenia muiticaps, Taenia serialis; Echinocuccus granulosus* and *Echinococcus granulosus* and *Echinococcus multilocularis*, as well as *Multiceps muiticaps*.

The compounds of formula I are also suitable for the control of *Coccidiose*, which can appear especially on piglets and chickens. Apart from *Coli* bacteria and *Clostridiae, Coccidiae* are one of the most important causes of diarrhoea of unweaned piglets. The most important type in the case of piglets is *isospora suis*. The piglets become infected with the oocysts (spores) of *isospora suis* through the mouth. The oocysts migrate info the small Intestine, where they penetrate into the small intestinal mucosa. There, they pass through various stages of development. Between the fifth and ninth and the 11th to 14th day after infection, the *Coccidiae* emerge from the intestinal mucosa and are then detectable again in the faeces. This outbreak causes great damage to the Intestinal mucosa. The piglets react by exhibiting partly yellowish—pasty to watery diarrhoea, it has a rancid small. Occasionally, individual piglets vomit. It is customary for the diarrhoea to occur between the eighth and fifteenth day of age.

Most particularly, *Taenia hydatigena, T. pisiformis, T. ovis, T, taeniaeformis, Multiceps multiceps, Joyeuxiella pasquali, Dipylidium caninum, Mesocestoides* spp., *Echinococcus granulosus* and *E. multilocularis* are controlled on or in dogs and cats simultaneously with *Dirofilaria immitis, Ancylostoma* ssp., *Toxocara* ssp. and/or *Trichuris vulpis*. Equally preferred, *Ctenocephalides felis* and/or *C. canis* are simultaneously controlled with the above-mentioned nematodes and cestodes.

Furthermore, the compounds of formula I are suitable for the control of human pathogenic parasites. Of these, typical representatives that appear in the digestive tract are those of the species *Ancylostoma, Necator, Ascaris, Strongyloides, Trichinella, Capillaria, Trichuris* and *Enterobius*. The compounds of the present invention are also effective against parasites of the species *Wuchereria, Brugia, Onchocerca* and *Loa* from the family of Filariidae, which appear in the blood, in the tissue and in various organs, and also against Dracunculus and parasites of the species *Strongyloides* and *Trichinella*, which infect the gastrointestinal tract in particular.

In addition, the compounds of formula 1 are also effective against harmful and pathogenic fungi on humans and animals.

The good pestieidal activity of the compounds of formula I according to the invention corresponds to a mortality rate of at least 50-60% of the pests mentioned. In particular, the compounds of formula I are notable for the exceptionally long duration of efficacy. The compounds of formula I are preferably employed in unmodified form or preferably together with the adjuvants conventionally used in the art of formulation and may therefore be processed in a known manner to give, for example, emulsifiable concentrates, directly dilutable solutions, dilute emulsions, soluble powders, granules or microencapsulations in polymeric substances. As with the compositions, the methods of application are selected in accordance with the intended objectives and the prevailing circumstances.

The formulation, i.e. the agents, preparations or compositions containing the active ingredient of formula I, or combinations of these active ingredients with other active ingredients, and optionally a solid or liquid adjuvant, are produced in a manner known per so, for example by intimately mixing and/or grinding the active ingredients with spreading compositions, for example with solvents, solid carriers, and optionally surface-active compounds (surfactants).

The solvents in question may be; alcohols, such as ethanol, proparsol or butanol, and glycols and their ethers and esters, such as propylene glycol, dipropyiene glycol ether, ethylene glycol, ethylene glycol mono-methyl or -ethyl ether, ketones, such as cyclohexanona, isophorone or diacetanol alcohol, strong polar solvents, such as N-methyl-2-pyrrolidone, dimethyl sulfoxide or dimethylformarnide, or water, vegetable oils, such as rape, castor, coconut, or soybean oil, and also, if appropriate, silicone oils.

Preferred application forms for usage on warm-blooded animals in the control of helminths include solutions, emulsions, suspensions (drenches), food additives, powders, tablets including effervescent tablets, boil, capsules, micro-capsules and pour-on formulations, whereby the physiological compatibility of the formulation excipients must be taken into consideration.

The binders for tablets and boll may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, macrocrystalline cellulose, sugar, lactose etc.), glidants and disintegrants.

If the anthelminthics are present in the form of feed concentrates, then the carriers used are e.g. performance feeds, feed grain or protein concentrates. Such feed concentrates or compositions may contain, apart from the active ingredients, also additives, vitamins antibiotics, chemotherapeutics or other pesticides, primarily bacteriostats, fungistats, coccidiostats, or even hormone preparations, substances having anabolic action or substances which promote growth, which affect the quality of meat of animals for slaughter or which are beneficial to the organism in another way. If the compositions or the active ingredients of formula I contained therein are added directly to feed or to the drinking troughs, then the formulated feed or drink contains the active ingredients preferably In a concentration of ea. 0.0005 to 0.02 % by weight (5-200 ppm).

The compounds of formula I according to the invention may be used alone or in combination with other biocides. They may be combined with pesticides having the same sphere of activity e.g, to increase activity, or with substances having another sphere of activity e.g. to broaden the range of activity. It can also be sensible to add so-called repellents. If the range of activity is to be extended to endoparasites, e.g. warmers, the compounds of formula I are suitably combined with substances having endoparasitic properties. Of course, they can also be used in combination with antibacterial compositions. Since the compounds of formula I are adulticides, i.e. since they are effective in particular against the adult stages of the target parasites, the addition of pesticides which instead attack the Juvenile stages of the parasites may be very advantageous. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula I.

Suitable partners in the mixture may be blocides, e.g. the insecticides and acaricides with a varying mechanism of activity, which are known to the person skilled in the art, e.g, chitin synthesis inhibitors, growth regulators; active ingredients which act as juvenile hormones; active ingredients which act as adulticides; broad-band insecticides, broad-band acaricldes and nematicides; and also the well known anthelmintics and Insect- and/or acarid-deterring substances, repellents, detachers and synergists.

Non-limitative examples of suitable insecticides and acaricides are mentioned in WO 2009/071500, compounds Nos. 1-284 on pages 18-21.

Non-limitative examples of suitable anthelmintics are mentioned in WO 2009/071500, compounds (A1)-(A31) on page 21.

Non-limitative examples of suitable repellents and detachers are mentioned in WO 2009/071500, compounds (R1)-(R3) on page 21 and 22.

Non-limitative examples of suitable synergists are mentioned in WO 2009/071500, compounds (S1)-(S3) on page 22.

Accordingly, a further essential aspect of the present invention relates to combination preparations for the control of parasites on warm-blooded animals, characterised in that they contain, in addition to a compound of formula I, at least one further active ingredient having the same or different sphere of activity and at least one physiologically acceptable carrier. The present invention is not restricted to two-fold combinations.

In one embodiment of the invention, the compound of formula I is used in combination with one or more further anthelmintic agents. Such a combination may reduce further the likelihood of resistance developing. Suitable further anthelmintic agents include:

(A) a macrocyclic lactone, for example ivermectin, avermectin, abamectin, emamectin, eprinomectin, doramectin, selamectin, moxidectin, nemadectin, milbemycin or a derivative thereof, for example milbemycin oxim.

Particularly preferred combinations according to this embodiment comprise:
(ia) a compound according to formula I above and doramectin;
(ib) a compound according to formula I above and milbemycin oxim;
(ic) a compound according to formula I above and abamectin;
(iia) the (1S)-enantiomer of a compound of formula I above and doramectin;
(iib) the (1S)-enantiomer of a compound of formula I above and milbemycin oxim;
(iic) the (1S)-enantiomer of a compound of formula I above and abamectin;
(iii) the compound N-[1-cyano-2-(5-cyano-2-{2-chloro-4-trifluoromethoxyphenoxy}-phenoxyl-1-methylethyl]-4-trifluoromethoxybenzamide and doramectin;
(iv)) the compound N-[1-cyano-2-(5-cyano-2-{2-chloro-4-trifluoromethoxyphenoxy}-phenoxy-1-methylethyl]-4-trifluoromethoxybenzamide and milbemycin oxim;
(v) the compound N-[1-cyano-2-(5-cyano-2-{2-chloro-4-trifluoromethoxyphenoxy)-phenoxy)-1methylethyl]-4-trifluoromethoxybenzamide and abamectin;
(vi) the compound N-[1-cyano-2-(5-cyano-2-{2-chloro-4-trifluoromethoxyphenoxy}-phenoxy)-1-methylethyl]-4-trifluoromethylsulfonylbenzamide and doramectin;
(vii) the compound N-[1-cyano-2-(5-cyano-2-{2-chloro-4-trifluoromethoxyphenoxy}-phenoxy)-(1-methylethyl]-4-trifluoromethylsulfonylbenzamide and milbemycin oxim;
(viii)) the compound N-[1-cyano-2-(5-cyano-2-{2-chloro-4-trifluoromethoxyphenoxy}-phenoxy)-(1-methylethyl]-4-trifluoromethylsulfonylbenzamide and abamectin;
ix) the enantiomer N-[(1S)-1-cyano-2-(5-cyano-2-{2-chloro-4-trifluoromethoxyphenoxy}-phenoxy)-1-methylethyl]-4-trifluoromethoxybenzamide and a macrocydic lactone selected from ivermectin, avermectin, abamectin, emamectin, eprinomectin, doramectin, selamectin, moxidectin, nemadectin and milbemycin oxim;
(x) the enantiomer N-[(1S)-1-cyano-2-(5-cyano-2{2-chloro-4-trifluoromethoxyphenoxy}-phenoxy)-1-methylethyl]-4-trifluoromethylsulfonylbenzamide and a macrocyclic lactone selected from ivermectin, avermectin, abamectin, emamectin, eprinomectin, doramectin, selamectin, moxidectin, nemadectin and milbemycin oxim;
(xi) the enantiomer N-[(1S)-1-cyano-2-(5-cyano-2-{2-chloro-4-trifluoromethoxyphenoxy}-phenoxy)-1-methylethyl]-4-trifluoromethoxybenzamide and doramectin;
(xii) the enantiomer N-[(1S)-1-cyano-2-(5-cyano-2-{2-chloro-4-trifluoromethoxyphenoxy}-phenoxy)-1-methylethyl]-4-trifluoromethoxybenzamide and milbemycin oxim;
(xiii) the enantiomer N-[(1S)-1-cyano-2-(5-cyano-2-{2-chloro-4-trifluoromethoxyphenoxy}-phenoxy)-1-methylethyl]-4-trifluoromethylsulfonylbenzamide and doramectin;
(xiv) the enantiomer N-[(1S)-1-cyano-2-(5-cyano-2-{2-chloro-4-trifluoromethoxyphenoxy}-phenoxy)-1-methylethyl]-4-trifluoromethylsulfonylbenzamide and milbemycin oxim.

(B) a benzimidazole, for example albendazole, cambendazole, fenbendazole, flubendazole, mebendazole, oxfendazole, oxibandazole or parbendazole.

(C) an imidazothiazole or tetrahydropyrimidine, for example tetramisole, levamisole, pyrantel, pamoate, oxantel or morantel.

Particularly preferred combinations according to this embodiment comprise:
(i) a compound according to formula I above and levamisole;
(ii) the (1S)-enantiomer of a compound of formula I above and levamisole;
(iii) the compound N-[1-cyano-2-(5-cyano-2-{2-chloro-4-trifluoromethoxyphenoxy}-phenoxy)-1-methylethyl]-4-trifluoromethoxybenzamide and levamisole;
(iv) the compound N-[1-cyano-2-(5-cyano-2-{2-chloro-4-trifluoromethoxyphenoxy}-phenoxy)-1-methylethyl]-4-trifluoromethylsulfonylbenzamide and levamisole;

(v) the enantiomer N-[(1S)-1-cyano-2-(5-cyano-2-{2-chloro-4-trifluoromethoxyphenoxy}-phenoxy)-1-methylethyl]-4-trifluoromethoxybenzamide and levamisole;
(vi) the enantiomer N-[(1S)-1-cyano-2-(5-cyano-2-{2-chloro-4-trifluoromethoxyphenoxy}-phenoxy)-1-methylethyl]-4-trifluoromethylsulfonylbenzamide and levamisole;
(D) a cyclic depsipeptide, for example emodepside.
(E) paraberquamide A or a derivative or analogue thereof.

Paraberquamide A, CAS Registry Number 77392-58-8, has the structure of formula (H)

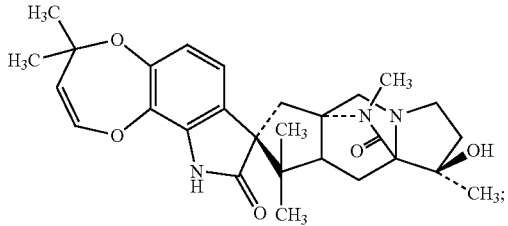

(II)

and the chemical name: [1'R-(1'α,5'aβ,7'β, 8'aβ,9'aβ)]-2',3',8'a, 9'-tetrahydro-1'-hydroxy-1',4,4,8',8',11'-hexamethyl-spiro[4H-8H-[1,4]dioxepino[2,3-g]indole-8,7'(8'H)-[5H,6H-5a,9a](iminomethano)[1H]cyclopent[f]indolizine]-9,10'(10H)-dione.

Paraherquamide A is commercially available; the compound may be isolated, for example, as a fungal metabolite of *Penicillium paraherquei*, now usually called *Penicillium brasilianum*, using standard fermentation and isolation techniques. Further *Penicillium* species have been described to produce the compound.

Suitable derivatives of paraberquamide A useful in combination with a compound of formula I are, for example,
(E1) dihydroparaherquamide, the compound of formula

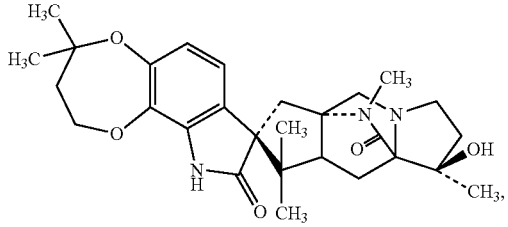

(IIa)

obtainable from, paraberquamide A, for example, by catalytic hydrogenation over palladium on a carbon support, as disclosed, for example, in EP-A-31742 A; or
(E2) 2-deoxoparaherquamide, the compound of formula

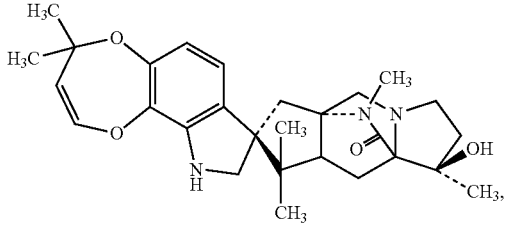

(IIb)

which has the chemical name derquantel or (1'R-(1'α,5'aβ, 7'β, 8'aβ,9'aβ)]-2',3',8'a,9,9', 10-hexahydro-1'-hydroxy-1',4, 4,8',8',11'-hexamethylspiro[4H,8H-[1,4]dioxepino[2,3-9]in-dole-8,7'(8')-[5H,6H-5a,9a](iminomethano)[1H]cyclopent [f]indolizine]-10'-one. 2-deoxo-paraherquamide is known, for example, from U.S. Pat. No. 5,750,695, and may be obtained according to the processes described therein.

Suitable analogues of paraberquamide A are, for example, the marcfortines; Examples are Marcfortine A, known from J. Chem. Soc. Chem. Commun. 1980, 601-602, or Marcfortines B and C, known from Tetrahedron Letters 22, 1977-1980 (1981).

Particularly preferred combinations according to this embodiment, comprise:
(i) a compound according to formula I above and paraberquamide A;
(ii) a compound according to formula I above and 2-deoxoparaberquamide;
(iii) the (1S)-enantiomer of a compound of formula I above and paraberquamide A;
(iv) the (1S)-enantiomer of a compound of formula I above and 2-deoxoparaherquamide;
(v) the compound N-[1-cyano-2-(5-cyano-2-{2-chloro-4-trifluoromethoxyphenoxy}-phenoxy)-1-methylethyl]-4-trifluoromethoxybenzamide and paraherquamide A;
(vi) the compound N-[1-cyano-2-(5-cyano-2-{2-chloro-4-trifluoromethoxyphenoxy}-phenoxy)-1-methylethyl]-4-trifluoromethoxybenzamide and 2-deoxoparaberquamide;
(vii) the compound N-[1-cyano-2-(5-cyano-2-{2-chloro-4-trifluoromethoxyphenoxy}-phenoxy)-1-methylethyl]-4-trifluoromethylsulfonylbenzamide and paraherquamide A;
(viii) the compound N-[4-cyano-2-(5-cyano-2-{2-chloro-4-trifluoromethoxyphenoxy}-phenoxy)-1-methylethyl]-4-trifluoromethylsulfonylbenzamide and 2-deoxoparaherquamide;
(ix) the enantiomer N-[(1S)-1-cyano-2-(5-cyano-2-{2-chloro-4-trifluoromethoxyphenoxy}-phenoxy)-1-methylethyl]-4-trifluoromethoxybenzamide and paraherquamide A;
(x) the enantiomer N-[(1S)-1-cyano-2-(5-cyano-2-{2-chloro-4-trifluoromethoxyphenoxy}-phenoxy)-1-methylethyl]-4-trifluoromethoxybenzamideand 2-deoxoparaherquamide;
(xi) the enantiomer N-[(1S)-1-cyano-2-(5-cyano-2-{2-chloro-4-trifluoromethoxyphenoxy}-phenoxy)-1-methylethyl]-4-trifluoromethylsulfonylbenzamide and paraherquamide A;
(xii) the enantiomer N-[(1S)-1-cyano-2-(5-cyano-2-{2-chloro)-4-trifluoromethoxyphenoxy}-phenoxy)-1-methylethyl]-4-trifluoromethylsulfonylbenzamide and 2-deoxoparaherquamide.

In another embodiment of the invention, the compound of formula I is used in combination with one or more ectoparasiticidal compound. Suitable ectoparasiticidal compounds include:
(i) aryl pyrazoles, for example fipronil, pyriprole or pyraflu-prole;
(ii) pyrethroids;
(iii) insect growth regulators, for example lufenuron, fluaben-zuron;
(iv) spinosyns, for example spinosad, spinetoram;
(v) neonicotinoids, for example imidacloprid, dinotefuran; and
(vi) various other insecticides, for example metaflumizone, flubendiamide, indoxacarb, 4,6-bis-(4-fluoro-3-(trifluo-romethyl)phenoxy)-pyrimidin-5-ylamine and derivatives thereof as disclosed in WO2005/85211, 2-(3-N,N-dim-ethylamino-phenyl)-4,6-bis-(4-fluoro-3-trifluoromethyl-phenoxy)-pyrimidin-5-ylamine and derivatives thereof as disclosed in WO 2008/009891.

In case of mixtures of two or more active ingredients, the different active ingredients may be administered simultaneously, for example in a single dosage unit such as a single pour-on solution; sequentially or separately. Combinations of different active ingredients also may be presented in kit form.

As a rule, the anthelmintic compositions according to the invention contain 0.1 to 99 % by weight, especially 0.1 to 95 % by weight of active ingredient of formula I or mixtures thereof, 99.9 to 1% by weight, especially 99.8 to 5% by weight of a solid or liquid admixture, including 0 to 25% by weight, especially 0.1 to 25% by weight of a surfactant Application of the compositions according to the invention to the animals to be treated may take place topically, peroraiy, parenterally or subcutaneously, the composition being present, for example, in the form of a solution, emulsion, suspension, (drenche), powder, tablet, boli, capsule or pour-on- or spot-on formulation. Most preferably, the compositions of the present invention are applied orally or as an injectable, the compositions being present in the form of a solution, emulsion, suspension or suspoemulsion.

The pour-on or spot-on method consists in applying the compound of formula I to a specific location of the skin or coat, advantageously to the neck or backbone of the animal. This takes place e.g. by applying a swab or spray of the pour-on or spot-on formulation to a relatively small area of the coat, from where the active substance Is dispersed almost automatically over wide areas of the fur owing to the spreading nature of the components in the formulation and assisted by the animal's movements.

Examples of suitable carriers within the liquid formulations are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$-$C_{18}$; solutions of esters of dicarboxyiic acids, such as dibutyl phthalate, dlisopropyl isophthalate, adipic acid diisopropyl ester, di-n-butyl adipate or also solutions of esters of aliphatic acids, e.g. glycols. If may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides. In case of oily solutions, said solutions may include e.g. vegetable oils such as olive oil, groundnut oil, sesame oil, pine oil, linseed oil or castor oil.

The vegetable oils may also be present in epoxidised form. Paraffins and silicone oils may also be used.

Whereas it is preferred to formulate commercial products as concentrates, the end user will normally use dilute formulations.

Such compositions may also contain further additives, such as stabilisers, anti-foaming agents, viscosity regulators, binding agents or tackifiers, as well as other active ingredients, in order to achieve special effects.

Anthelmintic compositions of this type, which are used by the end user, similarly form a constituent of the present invention.

In each of the processes according to the invention for pest control or in each of the pest control compositions according to the invention, the active ingredients of formula I can be used in all of their steric configurations or in mixtures thereof.

The invention also includes a method of prophylaetically protecting warm-blooded animals, especially productive livestock, domestic animals and pets, against parasitic helminths, which is characterised in that the active ingredients of the formula or the active ingredient formulations prepared therefrom are administered to the animals as an additive to the feed, or to the drinks or also in solid or liquid form, orally or by injection or parenterally. The invention also includes the compounds of formula I according to the Invention for usage in one of the said processes.

The following Examples illustrate the invention further.

PREPARATION EXAMPLES

Example 1

N-[1-cyano-1-methyl-2-(5-cyano-2-{2-chloro-4-trifluoromethoxy-phenoxy}-phenoxy)-ethyl]-4-trifluoromethoxybenzamide [Compound No. 1.1]

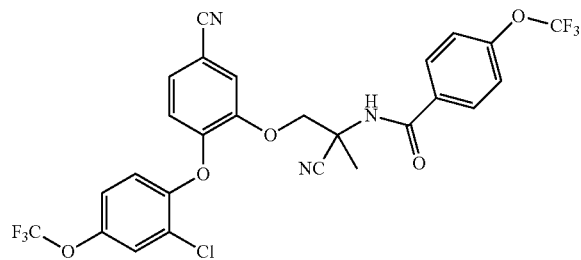 [SMILES: CC(C#N)(COc1cc(C#N)ccc1Oc1ccc(OC(F)(F)F)cc1Cl)NC(=O)c1ccc(OC(F)(F)F)cc1]

a) 18.3 g of 4-fluoro-3-methoxybenzonitrile, 30.0 g of of 2-chloro-4(trifluoromethoxy)phenol and 47.3 g of cesium carbonate are dissolved in 300 ml of dimethylformamide and stirred at 120° C. for 16 hours. After cooling the solution is diluted with diethyl ether, washed with water, a1N aqueous solution of sodium hydroxide, water and finally with brine. The organic phase is dried with magnesium sulfate and evaporated under vacuum. The crude 4-(2-chloro-4-trifluoromethoxy-phenoxy)-3-methoxy-benzonitrile is used in the step b) without further purification.

b) 30.6 g of product from step a) are dissolved in 150 ml of dichloromethane. The solution is cooled to 10° C. and 270 mL of a 1M solution of borontribromide in dichloromethane are slowly added over 30 min. The reaction mixture is then stirred for 20 hours at room temperature and poured into 1 liter of ice-cooled water. The phases are separated and the organic phase is washed with water and with brine. The organic phase is dried with magnesium sulfate and evaporated under vacuum. The crude 4-(2-chloro-4-trifluoromethoxy-phenoxy)-3-hydroxy-benzonitrile is used without further purification in step c).

c) 27.6 g of product from step b), 15 ml of chloroacetone, 17.4 g of potassium carbonate and 0.14 g of potassium iodide are dissolved in 300 mL of acetone and boiled under reflux for 4 hours. After cooling the precipitate is filtered and the filtrate is concentrated by evaporation, redissolved In ethylacetate and washed with 10% aqueous sodium thiosulfate, water and brine. The organic phase is dried with magnesium sulfate and evaporated under vacuum. The residue is crystallized from diethylether to yield 4-(2-chloro-4-trifluoromethoxy-phenoxy)-3-(2-oxo-propoxy)-benzonitrile.

d) 21.2 g of 4-(2-chloro-4-trifluoromethoxy-phenoxy)-3-(2-oxo-propoxy)-benzonitrile, 3.4 g of sodium cyanide and 3.7 g of ammonium chloride are suspended in 250 mL of ethanol, 170 mL of a 25% aqueous solution of ammonia are then added. The solution is stirred at room temperature for 16 hours and concentrated under vacuum. The residue is dissolved in ethyl acetate and washed with water and brine. The organic phase is dried with magnesium sulfate and evaporated under vacuum. The residue is recrystallized from ether/hexanes to yield 3-(2-amino-2-cyano-2-methyl-ethoxy)-4-(2-chloro-4-trifluomethoxy-phenoxy)-benzonitrile.

e) 24.0 g of 3-(2-amino-2-cyano-2-methyl-ethoxy)-4-(2-chloro-4-trifluoromethoxy-phenoxy)-benzonitrile and 12.0 mL of N, N-diisopropylamine are dissolved in 160 ml of dichloromethane and 14.2 g of 4-(trifluoromethoxy)-benzoylchloride are slowly added. The reaction mixture is stirred at room temperature for 20 hours and washed with water, with a 2M aqueous solution of hydrogen chloride, a saturated aqueous solution of sodium bicarbonate. The organic phase is dried with magnesium sulfate and evaporated under vacuum. The residue is purified by recrystallization from diethylether to yield the title compound as a colorless solid.

Example 2

N-[(1S)-1-cyano-2-(5-cyano-2-{2-chloro-4-trifluoromethoxyphenoxy}-phenoxy)-1-methylethyl]-4-trifluoromethoxybenzamide [Compound No. 1.2] and N-[(1R)-1-cyano-2-(5-cyano-2-{2-chloro-4-trifluoromethoxyphenoxy}-phenoxy)-1-methyl-ethyl]-4-trifluoromehoxy-benzamide [Compound No. 1.3]

Compound No 1.1 (2 g) is dissolved in a mixture dichloromethane and ethanol (20 ml) and the enantiomers are separated by preparative liquid chromatography (Gilson system, Chiralpak IC 200×50 mm, 20 µm, 60 mL/min, injection 2 ml) using n-heptane:dichloromethane:ethanol (70:25:5) as the mobile phase and UV detection. The appropriate fractions are combined and concentrated to give enantimerically pure compound No 1.2 (retention time 6.90 min, Chiralpak AD-H 150×4.6 mm, 5 µm, hexane:isopropanol 9:1, 1.2 mL/min, ee>99%) and compound No 1.3 (retention time 9.0 min, Chiralpak AD-H 150×4.6 mm, 5 µm, hexane:isopropanol 9:1, 1.2 mL/min, ee>99%)

Example 3

N-[1-cyano-1-methyl-2-(5-cyano-2-{2-chloro-4-trifluoromethoxy-phenoxy}-phenoxy)-ethyl]-4-trifluoromethylsulfanylbenzamide [Compound No. 1.7]

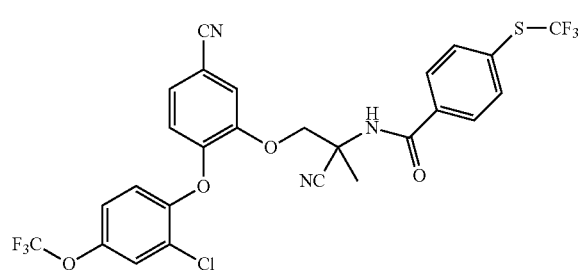 [SMILES: CC(C#N)(COc1cc(C#N)ccc1Oc1ccc(OC(F)(F)F)cc1Cl)NC(=O)c1ccc(SC(F)(F)F)cc1]

21.5 g of 3-(2-amino-2-cyano-2-methyl-ethoxy)-4-(2-chloro-4-trifluoromethoxy-phenoxy)-benzonitrile (described in example 1 step d)) and 11.4 ml of N, N-diisopropylamine are dissolved in 250 ml of dichloromethane and 14.5 g of 4-(trifluoromethylthio)-benzoylchloride are slowly added. The reaction mixture is stirred at room temperature for 20 hours and washed with water, a saturated aqueous solution of sodium bicarbonate and water. The organic phase is dried with magnesium sulfate and evaporated under vacuum. The residue is purified by recrystallization from diethylether/hexanes to yield N-[1-cyano-1-methyl-2-(5-cyano-2-{2-chloro-4-trifluoromethoxy-phenoxy}-phenoxy)-ethyl]-4-trifluoromethylsulfanyl-benzamide as a colorless solid.

Example 4

N-[1-cyano-1-methyl-2-(5-cyano-2-{2-chloro-4-trifluoromethoxy-phenoxy}-phenoxy)-ethyl]-4-trifluoromethylsulfonylbenzamide [Compound No. 1.12]

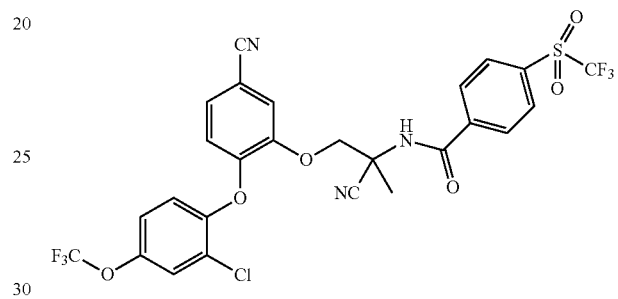

26.9 g of N-[1-cyano-1-methyl-2-(5-cyano-2-{2-chloro-4-trifluoromethoxy-phenoxy}-phenoxy)-ethyl]-4-trifluoromethylsulfanyl benzamide (described in example 3) are dissolved in a mixture of 500 ml acetonitrile, 120 ml of carbon tetrachloride and 200 mL of water and 28.0 g of sodium periodat and 450 mg of ruthenium trichlorid are added. The reaction mixture is stirred at room temperature for 1.5 hours and diluted with diethylether and water. The phases are separated and the organic phase is washed with water, a saturated aqueous solution of sodium bicarbonate and brine. The organic phase is dried with magnesium sulfate and evaporated under vacuum. The residue is purified by recrystallization from diethylether to yield the title compound as a pale grey solid.

The compounds named in Table 1 below may also be prepared analogously to the above-described method. The values of the melting points are given in ° C.

TABLE 1

| No. | Y | $X_1$ | $X_2$ | phys. data | configuration |
|---|---|---|---|---|---|
| 1.1 | O | Cl | $OCF_3$ | m.p. 120-121° C. | racemate |
| 1.2 | O | Cl | $OCF_3$ | foam | 1S enantiomer |
| 1.3 | O | Cl | $OCF_3$ | foam | 1R enantiomer |
| 1.4 | O | Cl | $CF_3$ | m.p. 122-124° C. | racemate |
| 1.5 | O | F | $CF_3$ | m.p. 107-108° C. | racemate |
| 1.6 | O | Br | $OCF_3$ | foam | racemate |

TABLE 1-continued

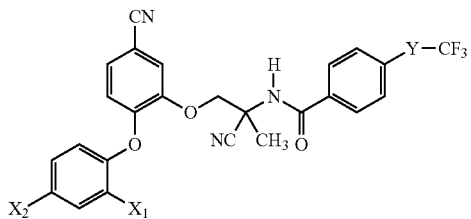

| No. | Y | $X_1$ | $X_2$ | phys. data | configuration |
|---|---|---|---|---|---|
| 1.7 | S | Cl | $OCF_3$ | m.p. 136-137° C. | racemate |
| 1.8 | S | Cl | $CF_3$ | m.p. 137-138° C. | racemate |
| 1.9 | S | F | $CF_3$ | m.p. 128-129° C. | racemate |
| 1.10 | S | Br | $OCF_3$ | m.p. 140-142° C. | racemate |
| 1.11 | SO | Cl | $OCF_3$ | m.p. 132-134° C. | racemate |
| 1.12 | $SO_2$ | Cl | $OCF_3$ | m.p. 128-130° C. | racemate |
| 1.13 | $SO_2$ | Cl | $OCF_3$ | foam | 1S enantiomer |
| 1.14 | $SO_2$ | Cl | $OCF_3$ | foam | 1R enantiomer |

Biological Examples

1. Activity In Vitro Against *Trichostrongylus colubriformis* and *Haemonchus contortus* (LDA Test)

Freshly harvested and cleaned nematode eggs are used to seed a suitably formatted 96-well plate containing the test substances to be evaluated for antiparasitic activity. Each compound is tested by serial dilution in order to determine its MBQ The test compounds are embedded in an agar-based nutritive medium allowing the full development of eggs through to third instar larvae. The plates are incubated for 8 days at 25° C. and 80% relative humidity (RH). Egg-hatching and ensuing larval development are: recorded to identify a possible nematodicidal activity. Efficacy is expressed in percent reduced egg hatch, reduced development of L3, or paralysis & death of larvae of all stages.

The following compounds from Table 1 show more than 90% ($EC_{90}$) efficacy against both worms at 0.1 ppm: 1.1, 1.2, 1.4-1.13

2. In-vivo Test on *Trichostrongylus colubriformis* and *Haemonchus contortus* in Mongolian Gerbils (*Meriones unquiculatus*) Using Peroral Application Six to eight week old Mongolian gerbils are infected through a stomach tube with ca. 2000 third instar larvae each of *T. colubriformis* and *H contortus*. 6 days after infection, the gerbils are treated by peroral application with the test compounds, dissolved in a mixture of 2 pasts DMSO and 1 part polyethylene glycol (PEG 400). On day 9 (3 days after treatment), when most of the *H. cantortus* that are still present are late 4th instar larvae and most of the *T. colubriformis* are immature adults, the gerbils are killed in order to count the worms. The efficacy is calculated as the % reduction of the number of worms in each gerbil, compared with the geometric average of number of worms from 6 infected and untreated gerbils.

In this test, a vast reduction in nematode infestation is achieved with the compounds of formula I. in particular, at a dose of 0.32 mg/kg compounds 1.1, 1.4, 1.3 and 1.7 from Table 1 each show a 100% efficacy and compound 1.12 a 98% efficacy against both worms.

3. In-Vivo Test on *Teladorsagia circumcincta* in Sheep Using Peroral Application Sheep are infected with 6,000 to 8,000 third stage larvae of *Teladorsagia circumcincta* (Tca) 7 to 5 days prior to treatment Animals in the treated groups are treated orally at a dose of 2 or 5 mg per kg bodyweight. Control animals do not receive any treatment. The animals are euthanized 19 to 21 days after treatment and the worm burden in the abomasum is examined. Efficacy assessment of the compounds is determined by comparison of the treated and untreated groups worm counts, calculated using Abbott's formula as follows:

% efficacy=100×(C−T)/C, where C is the geometric mean worm count of each species for the untreated control group and T, the geometric mean worm count of each species for the treated group.

Results for some compounds from Table 1 are shown in Table 2:

| Compound | Dose (mg/kg) | Efficacy against Tca [%] |
|---|---|---|
| Example 1.1 | 2 | 99 |
| Example 1.4 | 2 | 88 |
| Example 1.5 | 2 | 96 |
| Example 1.7 | 2 | 99 |
| Example 1.12 | 2 | 99 |
| Comparative Example WO 2005/058002, Example 1.47 | 5 | 0 |

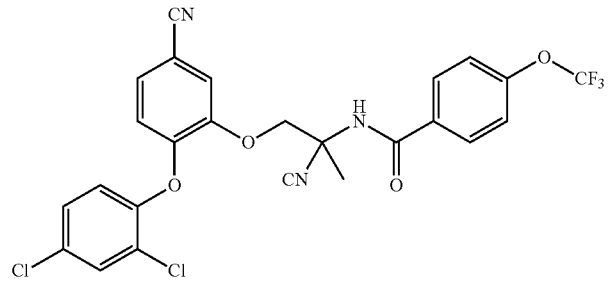

| Compound | Dose (mg/kg) | Efficacy against Tca [%] |
|---|---|---|
| Comparative Example WO 2003/104187, Example 1.62 | 5 | 15 |

4. In-vivo Test on *Ostertagia ostertagi* in Cattle Using Peroral Application

Cattle are infected with 7,000 to 10,000 third stage larvae of *Ostertagia ostertagi* (Oo) 7 to 5 days prior to treatment. Animals in the treated groups are treated orally at a dose of 5 or 20 mg per kg bodyweight Control animals do not receive any treatment. The animals are euthanized 23 to 28 days after treatment and the worm burden in the abomasum is examined. Efficacy assessment of the compounds is determined by comparison of the treated and untreated groups worm counts, calculated using Abbott's formula as follows: % efficacy=100×(C−T)/C; where C is the geometric mean worm count of each species for the untreated control group and T, the geometric mean worm count of each species for the treated group.

Results for some compounds from Table 1 are shown In Table 3:

| Compound | Dose (mg/kg) | Efficacy against Oo [%] |
|---|---|---|
| Example 1.1 | 5 | 100 |
| Example 1.4 | 5 | 100 |
| Example 1.7 | 5 | 100 |
| Example 1.12 | 5 | 100 |
| Comparative Example WO 2005/058805, Example 1.47 | 20 | 55 |

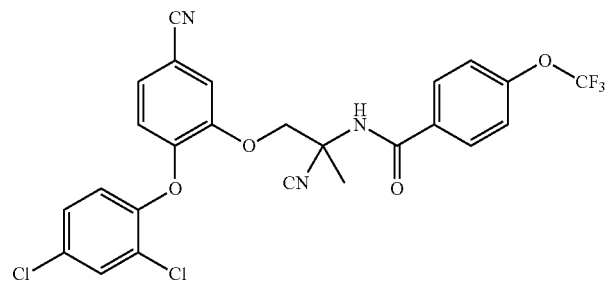

What we claim is:

1. A compound of formula

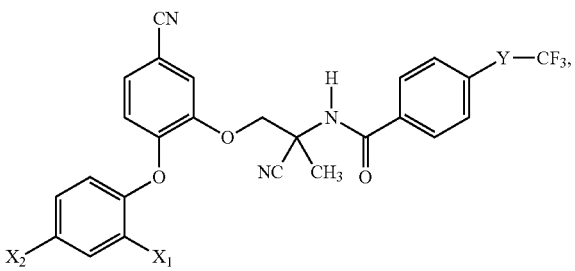

I wherein
X₁ is halogen;
X₂ is $CF_3$ or $OCF_3$, and
Y is O, S, S(O) or $S(O_2)$.

2. A compound of formula I according to claim 1, wherein Y is O, S or $S(O_2)$.

3. A compound of formula I according to claim 1, wherein Y is O.

4. A compound of formula I according to claim 1, wherein Y is $S(O_2)$.

5. A compound of formula I according to claim 1, wherein X₁, is Cl.

6. A compound of formula I according to claim 1, wherein X₂ is $CF_3$ or $OCF_3$.

7. A compound of formula I according to claim 1, wherein X₁ is Cl, X₂ is $OCF_3$ and Y is O, S, S(O) or $S(O_2)$.

8. A compound of formula I according to claim 1, which is
N-[1-cyano-2-(5-cyano-2-{2-chloro-4-trifluoromethoxyphenoxy}-phenoxy)-1-methylethyl]-4-trifluoromethoxybenzamide; or
N-[1-cyano-2-(5-cyano-2-{2-chloro-4-trifluoromethoxyphenoxy }-phenoxy)-1-methylethyl]-4-trifluoromethylsulfanylbenzamide; or
N-[1-cyano-2-(5-cyano-2-{2-chloro-4-trifluoromethoxyphenoxy}-phenoxy)-1-methylethyl]-4-trifluoromethylsulfinylbenzamide; or
N-[1-cyano-2-(5-cyano-2-{2-chloro-4-trifluoromethoxyphenoxy}-phenoxy)-1-methylethyl]-4-trifluoromethylsulfonylbenzamide.

9. An (1S)-enantiomer of a compound of formula I according to claim 1.

10. A Composition for the control of parasites, which contains as active ingredient at least one compound of formula I according to claim 1, in addition to carriers and/or dispersants.

11. A Method of controlling parasites, wherein an effective amount of at least one compound of formula I according to claim 1 is used on the parasites.

* * * * *